United States Patent [19]

Howard

[11] 4,391,390
[45] Jul. 5, 1983

[54] CHEMICAL-MIXING AND DISPENSING APPARATUS

[76] Inventor: Arthur G. Howard, 7711 Newport Way, Apt. D., Indianapolis, Ind. 46250

[21] Appl. No.: 226,894

[22] Filed: Jan. 21, 1981

[51] Int. Cl.³ ............................................. B05B 7/26
[52] U.S. Cl. .................... 222/136; 222/145; 222/395; 137/205.5; 239/310
[58] Field of Search ...................... 222/136, 145, 395; 239/310, 317; 137/205.5

[56] References Cited

U.S. PATENT DOCUMENTS

| | | | |
|---|---|---|---|
| 1,560,044 | 11/1925 | Derrick | 137/568 X |
| 2,219,763 | 10/1940 | Cartier et al. | 222/395 X |
| 3,451,402 | 6/1969 | Howard | 137/88 X |
| 3,690,340 | 9/1972 | Sipin | 137/205.5 X |
| 3,712,513 | 1/1973 | Ashmead et al. | 137/205.5 X |
| 3,823,727 | 7/1974 | Fry | 137/88 |
| 4,004,884 | 1/1977 | Zdrodowski | 137/88 X |
| 4,162,689 | 7/1979 | Zdrodowski | 137/88 X |

FOREIGN PATENT DOCUMENTS 369910 7/1963 Switzerland ............ 137/205.5

Primary Examiner—Joseph J. Rolla
Assistant Examiner—Frederick R. Handren
Attorney, Agent, or Firm—Woodard, Weikart, Emhardt & Naughton

[57] ABSTRACT

A chemical-mixing and dispensing apparatus for providing a volume of a chemical mixture to a dispensing location includes a suitably connected and monitored water main flow coupled to one inlet of a Tee fitting, a fixed-volume container having therein a liquid detergent concentrate, the container being coupled to the other inlet of the Tee fitting. The outlet of the Tee fitting is placed in flow communication with a chemical mixture holding tank along one branch and with a control tank along another branch. The chemical mixture holding tank has an output line which is monitored by an electrically timed solenoid valve for controlling the dispensing of the contents of the holding tank to a spray nozzle. Flow to the control tank is monitored by a pressure regulator such that the pressure ceiling within the control tank remains at a level which is below the pressure ceiling of the holding tank. The control tank is coupled to the fixed volume container such that as flow from the control tank enters the fixed-volume container, equal volume of detergent concentrate is pushed out. Due solely to pressure differences created within the flow loop, caused by dispensing of the mixture from the mixture holding tank, flows of both liquid detergent concentrate and water occur and these flows are mixed by the Tee fitting.

12 Claims, 1 Drawing Figure

CHEMICAL-MIXING AND DISPENSING APPARATUS

BACKGROUND OF THE INVENTION

This invention relates in general to apparata designed to dispense chemicals at a remote location. More specifically, the present invention relates to apparata which mix two or more chemicals in desired proportions and then control the dispensing of the resultant mixture. Chemical-blending and dispensing apparata, while old in the art, generally fall into one of two design styles or categories. The first category includes those apparata wherein the metering of chemicals to be mixed together is governed by the extent or degree that a control valve is opened. A conventional water faucet is representative of this type of control valve. One drawback with this type of device is the inherent inaccuracy in volume control. Typically, the degrees of rotation of the knob do not accurately correlate to the volume flow rate. Another drawback involves the limitations on automatic ways to open and close the control valve and to control the extent or degree that the valve is opened.

The drawbacks associated with this first category of apparata are solved to some extent by the apparata of the second category. This second category includes those apparata which meter the chemicals to be mixed by electrical solenoid valves (or related devices). These types of valves are either fully opened or completely closed and the volume which flows through this valve is controlled solely by the length of time the valve remains open and the cross-sectional area of the valve passageway. Since the valves are either in an open or closed state, there are no intermediate settings to be concerned with. Since solenoid valves respond to electrical signals, their operation is fast, accurate and easily controlled. By the use of computers, microprocessors and related programming means, a large number of valves can be controlled and their operation managed in virtually an infinite number of ways and sequences. This type or category of device may be found in automated, chemical processing facilities wherein computers manage predominant portions of the production cycle.

Listed below are certain patent references which pertain to chemical-blending and dispensing devices. While each disclosed device may include certain novel aspects, none are believed anticipatory of the claimed invention.

| Patent No. | Patentee | Issue Date |
|---|---|---|
| 3,712,513 | Ashmead et al. | 1/23/73 |
| 3,451,402 | Howard | 6/24/69 |
| 4,162,689 | Zdrodowski | 7/31/79 |
| 1,560,044 | Derrick | 11/03/25 |
| 3,823,727 | Fry | 7/16/74 |
| 4,004,884 | Zdrodowski | 1/25/77 |

Ashmead et al. discloses an apparatus and method for gradient elution involving two separate supply sources of chemicals and means to proportion each chemical into a particular mixture. The introduction of each chemical into a mixing chamber is controlled by solenoid valves whose operation is controlled by electronic programming circuitry. The apparatus produces a supply of eluent having a precisely controlled time-varying concentration of each chemical.

Howard discloses a method of continuously blending a gasoline by operating a first engine on a target field and operating a second engine on a sample of the blended gasoline. The knock intensities of the target and sample fuels are compared to generate an error signal, and the error signal provides a basis for adjusting the relative portions of the components forming the blended gasoline. The apparatus employed includes time-controlled valves for introducing blending stocks A and B into a preliminary blending tank. The contents of this blending tank are then pumped to a final blending zone and from there to test engines.

Zdrodowski ('689) discloses a method for accurately controlling fluid flow rates utilizing time division control of pulse valves. The invention is particularly intended for controlling relatively low fluid flow rates such as 60 milliliters per hour or less. A pulse generator governs the control of three pulse valves, each of which corresponds to a different fluid reservoir. A gas line introduced into the top of each reservoir is used to evacuate the reservoirs of the various fluids when the pulse valves are opened.

Derrick discloses a liquid supply system including a pump, and a suction conduit extending from the pump to a source of supply. Also included is a discharge conduit leading from the pump to a remotely located faucet for discharge of the contents of the source of supply.

Fry discloses a foam cleaning system and a foam cleaner including control means actuated by build up of static pressure in a foaming chamber. This buildup of static pressure results in a cut-off of air pressure to the chamber thereby insuring that during periods when foam is not being produced, the pressure on the foamer hose is minimized.

Zdrodowski ('884) discloses a system for metering a plurality of fluids wherein time division switching of flow valves is used in order to provide accurate metering of a plurality of fluids from individual reservoirs. Gas lines connected to the top end of each fluid reservoir assist in evacuating those fluids from the reservoirs when the flow valves are opened.

Although time-controlled metering via solenoid valves is known in the art and frequently employed in devices, there are a number of drawbacks. For example, the accuracy of the device depends upon the timer means employed, the reliability of the solenoid valves and the likelihood of component failures. These concerns are compounded by the fact that devices of this type are somewhat complex and may necessitate a comparatively large number of component parts for each chemical involved. While it is conceded that some timed controlled metering or dispersal of solution may not be able to be avoided entirely, it is believed beneficial to reduce the number of such time-controlled valves to the extent possible and the utility and desirability of a product is enhanced by the minimizing of such components.

The present invention represents a significant improvement over the prior art devices by providing a chemical-mixing and dispensing apparatus which is completely operable without the use of any timed, electrically-actuatable valves as part of the mixing of the various chemicals or solutions involved. Although some valve is desirable to control the delivery of the mixed chemicals to a remote-use location, the remainder of the apparatus operates solely on pressure differentials thereby performing a controlled blending without the expense and uncertainty of electrically controllable solenoid valves or other timed metering means.

SUMMARY OF THE INVENTION

A chemical-mixing and dispensing apparatus for providing a volume of solution to a dispensing location according to one embodiment of the present invention comprises a first chemical container having an inlet port and an outlet port, a first chemical disposed within the first chemical container, a source of a second chemical, a flow conduit in flow communication with the outlet port of the first chemical container and with the source of a second chemical, the flow conduit being arranged to allow simultaneous passage therethrough of the first and second chemicals, a fixed-volume chemical mixture holding tank having an outlet port in flow communication with the dispensing location and having an inlet port in flow communication with the flow conduit, a fixed-volume control tank in flow communication with and between the flow conduit and the inlet port of the first chemical container and flow control means for periodically releasing a portion of the contents of the chemical mixture holding tank to the dispensing location.

One object of the present invention is to provide an improved chemical-mixing and dispensing apparatus.

Related objects and advantages of the present invention will be apparent from the following description.

DESCRIPTION OF THE PREFERRED EMBODIMENT

Figure 1:
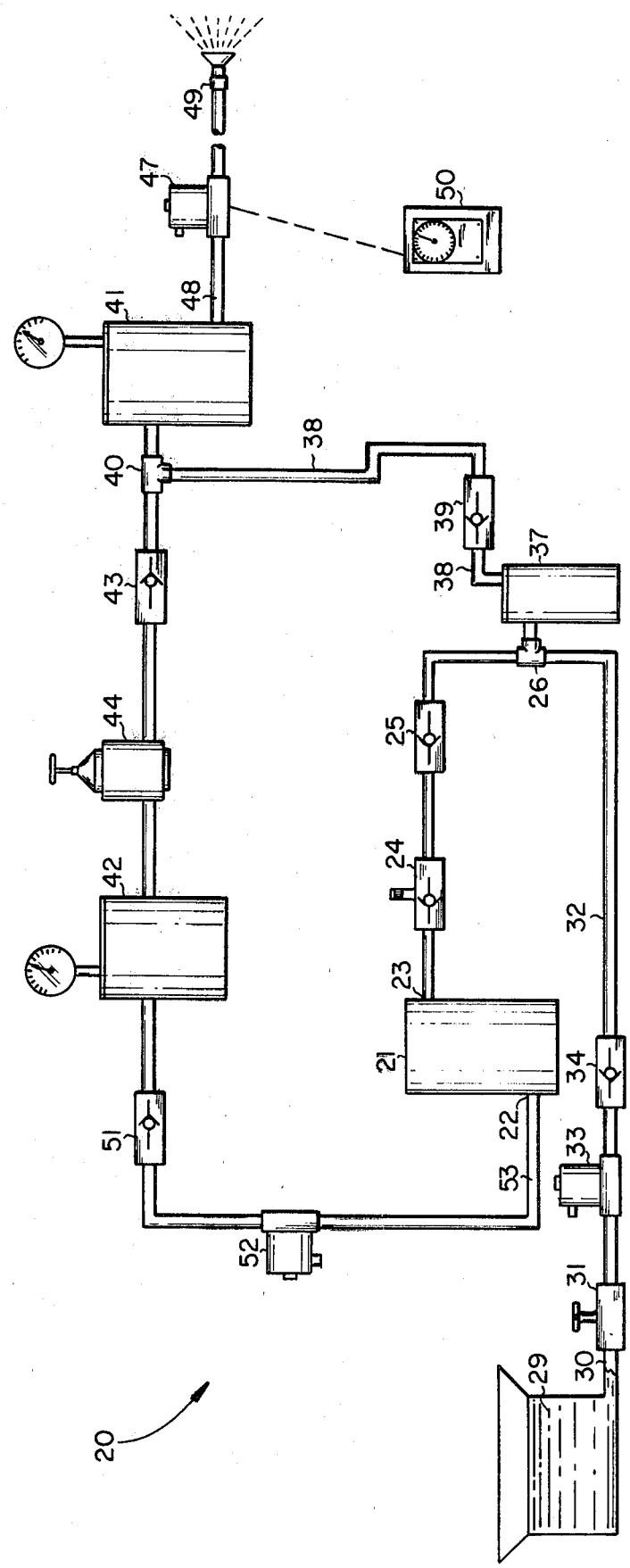
FIG. 1 is a diagrammatic illustration of a chemical-mixing and dispensing apparatus according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated, in diagrammatic form, chemical-mixing and dispensing apparatus 20. Apparatus 20 relates to the mixing and subsequent dispensing of two chemicals such as, for example, a detergent concentrate and water. Although these two chemicals will be discussed and referred to in the remainder of this text, it should be understood that these two chemicals have arbitrarily been selected for discussion of the exemplary embodiment and the teachings of this invention are equally applicable to virtually any two chemicals. Further, the apparatus disclosed is adaptable to the mixing-together of more than two chemical solutions.

Apparatus 20 includes a closed container 21 having a fixed volume of a first chemical initially placed, stored or loaded therein. In the exemplary embodiment, this first chemical is a liquid detergent concentrate. Container 21 has a lower inlet port at 22 and an upper outlet port at 23. Detergent concentrate exiting from the container flows through needle valve 24 and check valve 25 into one input side of Tee fitting 26 which has two input sides or locations and a single outlet location. In flow communication with the other input side of fitting 26 is a source 29 of a second chemical. In the exemplary embodiment, the second chemical is water and the source is a reservoir or tank providing water under pressure to residential and commercial users via water main 30.

As the pressurized flow of water is provided by the utility or water company, local users typically have a shut-off valve 31 and with this valve the local users may have certain filtering means, depending upon the intended use for the water which is provided. Such filtering may be provided in accompaniment with valve 31 or filtering may be accomplished at some other point in the delivery system. Although not a mandatory requirement of apparatus 20, line 32, which is an internal line to the structure wherein apparatus 20 is located, is equipped with a solenoid valve 33. Although this valve is illustrated as part of apparatus 20, it will be apparent from the description which follows that the system is operable in an equivalent manner without the presence of solenoid valve 33. Also provided in line 32 is check valve 34. In the event a second chemical other than water was selected for mixing, then the source of such chemical would likely be different than a reservoir and water main. However, the use of the second chemical only becomes of interest to apparatus 20 at the location of fitting 26. Thus, further discussions of how the second chemical gets to fitting 26, or what that particular second chemical may be, are not nearly as relevant as what happens to the two chemicals from fitting 26 on.

Fitting 26 represents a mixing location for the first and second chemicals. This fitting has a Tee shape and the single output branch is in flow communication with filter 37. While filter 37 is beneficial, it is not a requirement of apparatus 20. It should be understood that if filter 37 is eliminated from the apparatus, the output branch of fitting 26 goes directly into line 38. Also, if filter 37 is used and fitting 26 is eliminated, the two flow lines for the first and second chemicals go directly into filter 37 which then serves as the point of initial mixing for these two chemicals.

Positioned in line 38 is a check valve 39 and line 38 terminates at Tee fitting 40. One side of fitting 40 is coupled to storage tank 41 and the opposite side of fitting 40 is coupled to control tank 42. Flow from fitting 40 to control tank 42 passes through check valve 43 and pressure regulator 44. The output of storage tank 41 is controlled by solenoid valve 47 which is positioned in flow line 48 between tank 41 and spray nozzle 49. Spray nozzle 49 represents a dispensing location for the chemical mixture which is created upstream and temporarily stored in tank 41. The on-off cycling of solenoid valve 47 is controlled by electric timer 50, and a realistic duty cycle for the two selected chemicals and their intended use is no more than 10 seconds of detergent/water spray mist out of each 5-minute time interval. However, these on-off time period ratios are quite arbitrary and by selecting an adjustable timer, the cycling between on and off phases can be frequently and easily changed in order to adapt apparatus 20 to the particular requirements of the environment in which it is used.

The output of control tank 42 passes through check valve 51 and then through solenoid valve 52. Solenoid valve 52 is provided as a convenience factor to enable the changing of chemical in container 21. Whether a new chemical is being added or the same chemical is being replenished, without solenoid valve 52, the contents of tank 42 would drain out. In this regard, any manual shut-off would be acceptable in lieu of valve 52.

Line 53 couples tank 42 to the inlet port at 22. Since container 21 is a closed volume, the addition of solution from control tank 42 to the inlet port (located near the base of the container) forces out some of the chemical within the container via the outlet port at 23. In order to avoid mixing of the introduced solution and the stored first chemical, similarity of specific gravities is beneficial. With similar specific gravity values, the entering solution remains at the bottom of container 21 while the stored chemical within container 21 is pushed out without any significant degree of mixing occurring. Although there may be some slight mixing at the interface between the two solutions (chemicals), this is extremely minimal. Now that the structural aspects of apparatus 20 have been disclosed and described, the dynamic operation of the apparatus will now be discussed.

With solenoid valve 33 open, water (second chemical) which is under pressure due to the pressure in a water main, reaches fitting 26 and from that point passes through filter 37 and is ultimately introduced into tank 41. Tank 41 has a head of air and fills with water until the internal pressure in tank 41 equals that pressure within the water main. For purposes of discussion, assume that this pressure limit is 30 psi. Fitting 40 also allows water to fill tank 42. However, tank 42 in combination with pressure regulator 44 limits the pressure in tank 42 to 10 psi (roughly a 1:3 ratio with the pressure ceiling of tank 41). When both tanks are at their pressure ceilings, the apparatus arrives to a static, steady-state condition, the water which would otherwise enter through the water main is opposed by the back pressure present in tank 41. Since solenoid valve 47 is closed, the fluid stored within apparatus 20 soon reaches its maximum as to volume and pressure, and the apparatus is in a static condition. With tank 42 at 10 psi and tank 41 at 30 psi, there is a no-flow condition in lines 32 and 38 due to the pressure balance of the apparatus. There is no flow from container 21 due to the higher pressure at the outlet side of fitting 26. In this condition, solenoid valves 47 and 52 are closed and solenoid valve 33 is open.

When activated by electronic timer 50, solenoid valve 47 opens for a brief interval and discharges in a spray mist manner a portion of the chemical mixture presently being held in tank 41. This chemical mixture is immediately released through spray nozzle 49 and solenoid valve 52 opens simultaneously with solenoid valve 47 while solenoid valve 33 closes. The delivery of chemical mixture to nozzle 49 very rapidly drops the pressure in tank 41 which in turn creates a pressure drop upstream. This upstream pressure drop may drop as low as 5 psi and this creates a beneficial pressure differential between the first chemical within container 21 and fitting 26. Since valve 52 is opened, the 10 psi level in tank 42 seeks the lower pressure level at fitting 26. Consequently, a portion of the contents of tank 42 pass through open solenoid valve 52 and are introduced into container 21. The introduction of this volume of solution into container 21 forces a small amount of first chemical out of container 21 and on into fitting 26. Fitting 26 is internally divided so that neither the first chemical entering from one side nor the water entering from the other side will influence each other, while still enabling mixing at the outlet location. As the flow from tank 42 enters container 21 and the pressure differences achieve some degree of balance, electronic timer 50 goes to its off cycle and closes solenoid valves 47 and 52 while opening solenoid valve 33. A small amount of first chemical which has been pushed out of container 21 enters fitting 26 and is combined with a much larger volume of water which is now flowing due to the opening of solenoid valve 33. What has thus been created is a chemical mixture involving a very small volume of liquid detergent concentrate and a larger volume of water. This mixture then passes into filter 37 and from there on to tanks 41 and 42 as previously described.

The first chemical and water mixture begins to again fill both tanks 41 and 42. Since only a small portion of this mixture is first chemical, the majority is water. Since solenoid valve 47 has closed, the addition of this mixture begins to increase the pressure levels in tanks 41 and 42 and pushes their corresponding pressure levels toward their selected pressure ceilings. In a relatively short period of time the entire apparatus will again achieve its steady-state (static) condition. The apparatus then waits for timer 50 to return to its open (on) cycle at which time solenoid valves 47 and 52 open and solenoid valve 33 closes. The pressurized contents of tank 41, or at least a portion thereof, are sprayed through spray nozzle 49 and the pressure in the various lines drops. It is important to note that when the apparatus is initially filled, only water (second chemical) is involved. However, after one cycle, a portion of first chemical is introduced into the apparatus flow lines from container 21. Consequently, beginning with the second cycle, a mixture of the first and second chemicals is delivered from spray nozzle 49.

As the mixture is sprayed, the pressure in tank 41 drops and this pressure drop, as has been previously explained, thereby institutes certain flows to occur. Primarily, the flow from tank 42 into container 21 and from there on to fitting 26. Thus, it can be seen that the introduction of the first chemical into the system at which point it is mixed with a considerably larger volume of water is very accurately controlled on a pressure differential basis. Timed solenoid valves are not used for the metering of the two solutions which are desired to be mixed together into selected proportions.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A chemical-mixing and dispensing apparatus for providing a volume of a chemical mixture to a dispensing location, said chemical-mixing and dispensing apparatus comprising:
   a first chemical container having an inlet port and an outlet port;
   a first chemical disposed within said first chemical container;
   a source of a second chemical;
   flow conduit in flow communication with the outlet port of said first chemical container and with said source of a second chemical, said flow conduit allowing simultaneous passage therethrough of said first and second chemicals;
   a fixed-volume chemical mixture holding tank having an outlet port in flow communication with said dispensing location and having an inlet port in flow communication with said flow conduit;

a fixed-volume control tank in flow communication with and between said flow conduit and the inlet port of said first chemical container; and flow control means for periodically releasing a portion of the contents of said chemical mixture holding tank to said dispensing location.

2. The chemical-mixing and dispensing apparatus of claim 1 wherein all lines of flow communication between said first chemical container, said flow conduit, said chemical mixture holding tank and said control tank are free of any timed flow metering means.

3. The chemical-mixing and dispensing apparatus of claim 1 wherein said flow control means includes an electrically timed first solenoid valve located between the outlet port of said chemical mixture holding tank and said dispensing location, said first solenoid valve having a uniformly repeating on-off cycle.

4. The chemical-mixing and dispensing apparatus of claim 3 wherein said flow control means further includes a second solenoid valve located in the flow line between said control tank and the inlet port of said first chemical container, said second solenoid valve having an on-off cycle coinciding with the on-off cycle of said first solenoid valve.

5. The chemical-mixing and dispensing apparatus of claim 4 wherein said flow control means further includes a third solenoid valve located in the flow line between said source of said second chemical and said flow conduit, said third solenoid valve having an on-off cycle opposite to the on-off cycle of said first and second solenoid valves.

6. The chemical-mixing and dispensing apparatus of claim 1 wherein said first chemical is a detergent concentrate and said second chemical is water, said source of said second chemical including a water main providing a pressurized flow of water.

7. The chemical-mixing and dispensing apparatus of claim 1 wherein the flow line between said flow conduit and said control tank includes a pressure regulator, said pressure regulator being arranged to limit the internal pressure ceiling within said control tank to less than half of the internal pressure ceiling of said chemical mixture holding tank.

8. The chemical-mixing and dispensing apparatus of claim 1 wherein said flow conduit includes a Tee fitting having two separated inlets and a single outlet, said single outlet being in flow communication with the inlet port of said chemical mixture holding tank.

9. A chemical-mixing and dispensing apparatus for providing a volume of a chemical mixture to a dispensing location, said chemical-mixing and dispensing apparatus comprising:

a fixed-volume container having an inlet port and an outlet port, said outlet port being flow coupled to a mixing location;

a first chemical disposed within said fixed-volume container;

a volume of a second chemical flow coupled to said same mixing location;

flow delivery means cooperatively arranged with said volume of said second chemical for delivering said second chemical to said mixing location via a pressurized flow line;

a first holding tank flow coupled to said dispensing location;

a second holding tank flow coupled to said fixed-volume container, said first and second holding tanks being disposed in parallel flow communication with said mixing location, whereby chemical mixture flow from said mixing location branches into two flow paths, one in communication with said first holding tank and the other in communication with said second holding tank;

pressure regulating means associated with said second holding tank and being suitably adapted to limit the internal pressure ceiling within said second holding tank to a level below the internal pressure ceiling within said first holding tank;

a flow line connecting said second holding tank to the inlet port of said fixed-volume container; and a plurality of check valves suitably arranged in the various flow paths such that a pressure drop in said first holding tank allows said first and second chemicals to flow to said mixing location due solely to respective pressure differences.

10. The chemical-mixing and dispensing apparatus of claim 9 which further includes flow control means disposed between said first holding tank and said dispensing location for dispensing a portion of the contents of said first holding tank.

11. The chemical-mixing and dispensing apparatus of claim 10 wherein said flow control means includes an electrically timed solenoid having a uniformly repeating on-off cycle.

12. The chemical-mixing and dispensing apparatus of claim 9 wherein all lines of flow communicating between said mixing location and said first holding tank, said mixing location and said second holding tank, said second holding tank and said fixed-volume container and said fixed-volume container and said mixing location are free of any timed flow metering means.

* * * * *